US009127043B2

(12) United States Patent
Gronke et al.

(10) Patent No.: US 9,127,043 B2
(45) Date of Patent: Sep. 8, 2015

(54) PURIFICATION OF IMMUNOGLOBULINS

(75) Inventors: Robert S. Gronke, Boston, MA (US); Héctor Zaanoni, Boston, MA (US)

(73) Assignee: BIOGEN MA INC., Cambridge, MA (US)

( * ) Notice: Subject to any disclaimer, the term of this patent is extended or adjusted under 35 U.S.C. 154(b) by 61 days.

(21) Appl. No.: 13/254,697

(22) PCT Filed: Mar. 4, 2010

(86) PCT No.: PCT/US2010/026219
§ 371 (c)(1),
(2), (4) Date: Nov. 16, 2011

(87) PCT Pub. No.: WO2010/102114
PCT Pub. Date: Sep. 10, 2010

(65) Prior Publication Data
US 2012/0053325 A1    Mar. 1, 2012

Related U.S. Application Data

(60) Provisional application No. 61/157,850, filed on Mar. 5, 2009.

(51) Int. Cl.
*B01D 15/26* (2006.01)
*B01D 15/38* (2006.01)
*C07K 1/22* (2006.01)

(52) U.S. Cl.
CPC .............. *C07K 1/22* (2013.01); *B01D 15/3828* (2013.01); *B01D 15/26* (2013.01); *B01D 15/3804* (2013.01); *B01D 2015/3838* (2013.01)

(58) Field of Classification Search
None
See application file for complete search history.

(56) References Cited

U.S. PATENT DOCUMENTS

| 5,892,019 | A | 4/1999 | Schlom et al. |
| 8,017,740 | B2 * | 9/2011 | Gagnon ........................ 530/413 |
| 2008/0177048 | A1 | 7/2008 | Gagnon |

FOREIGN PATENT DOCUMENTS

| WO | WO 2008/086335 A2 | 7/2008 |
| WO | WO 2009/053358 A1 | 4/2009 |
| WO | WO 2009/053360 A1 | 4/2009 |
| WO | WO 2010/102114 A1 | 9/2010 |

OTHER PUBLICATIONS

Propylene Glycol (propylene glycol, retrieved from the Internet <http://en.wikipedia.org/wiki/Propylene_glycol>, retrieved on Sep. 23, 2013).*
Atkinson, T., et al., "Triazine-dye affinity chromatography," *Biochem. Soc. Trans.* 9:290-293, Portland Press on the Behalf of the Biochemical Society, United Kingdom (1981).
"Blue Sepharosem™ 6 Fast Flow," GE Healthcare Bio-Sciences Literature File No. 71-7055-00 AG, GE Healthcare Bio-Sciences AB, Sweden (2006), 16 pages.
Bruck, C., et al., "One-step purification of mouse monoclonal antibodies from ascitic fluid by DEAE Affi-gel blue chromatography," *J. Immunol. Methods* 53:313-319, Elsevier Science Publishers B.V. Netherlands (1982).
"Capto Blue," GE Healthcare Bio-Sciences Data File No. 28-9392-46 AA, GE Healthcare Bio-Sciences AB, Sweden (2008), 4 pages.
Clonis, Y. and Lowe, C., "Affinity chromatography on immobilised triazine dyes. Studies on the interaction with multinucleotide-dependent enzymes," *Biochim. Biophys.* Acta 659:86-98, Elsevier Publishing Co., Netherlands (1981).
Clonis, Y., "The applications of reactive dyes in enzyme and protein downstream processing," *Crit. Rev. Biotechnol.* 7:263-279, CRC Press, United States (1988).
Denizli, A. and Piskin, E., "Dye-ligand affinity systems," *J Biochem. Biophys. Methods* 49:391-416, Elsevier Science Publishers B.V., Netherlands (2001).
Emlen, W. and Burdick, G., "Purification of DNA antibodies using cibarcon blue F3GA affinity chromatography," *J Immunol. Methods* 62:205-215, Elsevier Science Publishers B.V., Netherlands (1983).
Gagnon, P. "Chapter 6: Purification of Monoclonal Antibodies by Mixed-Mode Chromatography," in *Process Scale Purification of Antibodies*, Gottschalk, U., ed., pp. 125-143, John Wiley & Sons, Inc., United States (2009).
Gagnon, P., and Gottschalk, U., cd., "The Emerging Generation of Chromatography Tools for Virus Purification," Supplement, BioProcess International 6:24-30, BioPress International, United States (2008).
Gagnon, P., et al., "Method for obtaining unique selectivities in ion-exchange chromatography by addition of organic polymers to the mobile phase," *J. Chromatography A* 743:51-55, Elsevier Science Publisher B.V., Netherlands (1996).
Gagnon, P., et al., "Nonionic polymer enhancement of aggregate removal in Ion Exchange and Hydroxyapatite chromatography," [Presentation] 12th Annual Waterside Conference, Apr. 23-25, 2007, San Juan, Puerto Rico.
Garg, N., et al., "Dye-affinity techniques for bioprocessing: recent developments," *J. Mol. Recognit.* 9:259-274, John Wiley & Sons, United Kingdom (1996).
Labrou, N., et al., "Chapter 9: Dyc-Ligand and Biomimetic Affinity Chromatography," in *Handbook of Affinity Chromatography, Chromatographic Science Series*, vol. 92, 2nd Ed., CRC Press, United States (2006).

(Continued)

*Primary Examiner* — Suzanne M Noakes
*Assistant Examiner* — Jae W Lee
(74) *Attorney, Agent, or Firm* — Sterne Kessler Goldstein & Fox P.L.L.C.

(57) ABSTRACT

The present invention pertains to improved methods of using dye-ligand affinity chromatography for the isolation of antibodies or proteins comprising an antibody fragment (such as Fc fusion proteins) from a mixture of undesirable contaminants. In particular, the use of an organic polymer such as polyethylene glycol (PEG) in the elution phase of an antibody/dye-ligand chromatography isolation procedure results in improved separation of target antibodies from undesirable contaminants. The methods described herein are particularly useful in separating or removing antibody aggregates, misfolded antibodies, and virus contaminants from target antibodies.

17 Claims, 13 Drawing Sheets

(56) References Cited

OTHER PUBLICATIONS

Figure 1:
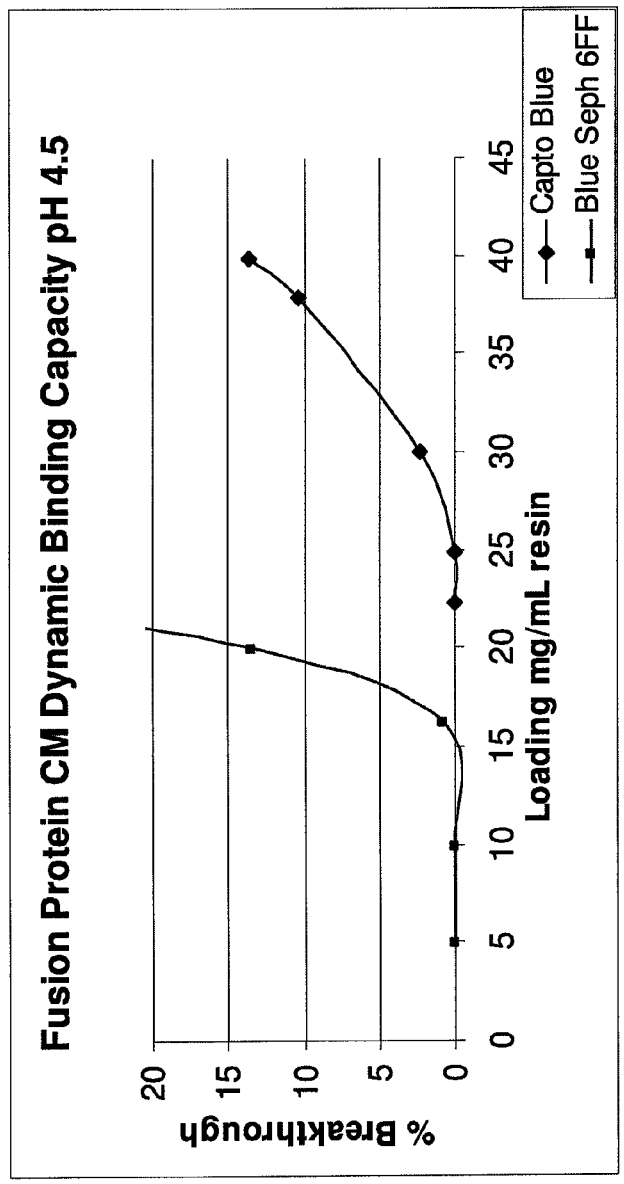

Prioli, R., et al., "Specific inhibition of *Trypanosoma cruzi* neuraminidase by the human plasma glycoprotein 'cruzin'," *Proc. Natl. Acad, Sci. USA* 84:3097-3101, National Academy of Sciences, United States (1987).

Scoble, J. and Scopes, R., "Well defined dye adsorbents for protein purification," *J. Mol. Recognit.* 9:728-732, John Wiley & Sons, United Kingdom (1996).

Shimakata, T. and Stumpf, P., "Fatty Acid Synthetase of *Spinacia oleracea* Leaves," *Plant Physiol.* 69:1257-1262, American Society of Plant Biologists, United States (1982).

Stellwagen, E., "Chromatography on immobilized reactive dyes," *Methods Enzymol.* 182:343-357, Academic Press, United States (1990).

Subranianian S., "Dye-ligand affinity chromatography: the interaction of Cibacron Blue F3GA® with proteins and enzymes," *Crit. Rev. Biochem.* 16:169-205, CRC Press, United States (1984).

Tucker, R., et al., "Protein Dye Affinity Chromatography Using Immobilized Tetraiodofluorescein," *J. Biol. Chem.* 256:10993-10998, American Society for Biochemistry and Molecular Biology, United States (1981).

Vlatakis G, et al., "Dye-ligand chromatography for the resolution and purification of restriction endonucleases," *Appl. Biochem. Biotechnol.* 15:201-212, Humana Press inc., United States (Oct. 1987).

International Search Report for International Patent Application No. PCT/US2010/026219, European Patent Office, Netherlands, mailed on Apr. 29, 2010.

Written Opinion of the International Searching Authority for International Patent Application No. PCT/US2010/026219, European Patent Office, Netherlands, mailed on Apr. 29, 2010.

Podestá, F. E., and Plaxton, W. C., "Activation of Cytosolic Pyruvate Kinase by Polyethylene Glycol," *Plant Physiol.* 103:285-88, American Society of Plant Biologists, United States (1993).

Riske, F., et al., "A potential generic downstream process using Cibracon Blue resin at very high loading capacity produces a highly purified monoclonal antibody preparation from cell culture harvest," *J Chromatogr. B* 848:108-15, Elsevier B.V., Netherlands (2007).

Jankowski, W., et al., "Binding of Human Interferons to Immobilized Cibacron Blue F3GA: The Nature of Molecular Interaction," *Biochem.* 15(23):5182-87, American Chemical Society, United States (1976).

\* cited by examiner

Binding capacity study comparing binding of an Fc-fusion protein on Blue Sepharose® versus Capto™ Blue

- Capto™ Blue dynamic binding capacity was 2 fold greater vs. Blue Sepharose®.
- Capacity is dependent on the pH of load and the pI of the molecule as capture is primarily driven by the cation exchange component.
*"CM"=clarified media.

NaCl gradient elution experiments showed poor resolution of aggregates and inactive forms
- 0.1-1.0M NaCl
  – AKTA® Chromatogram
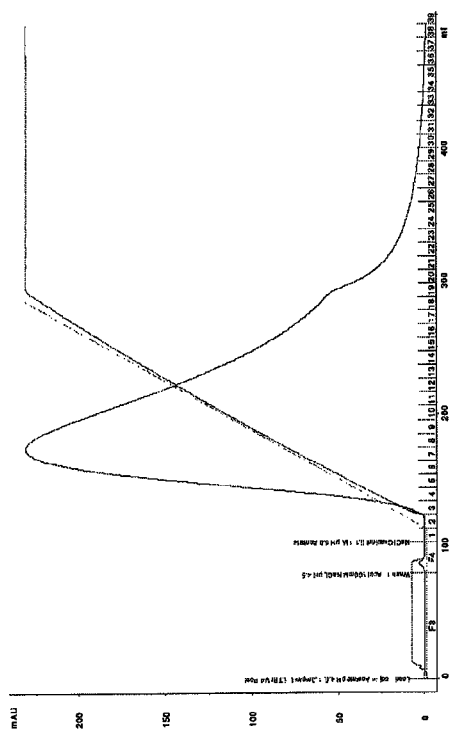
- Virtually no resolution observed with NaCl elution
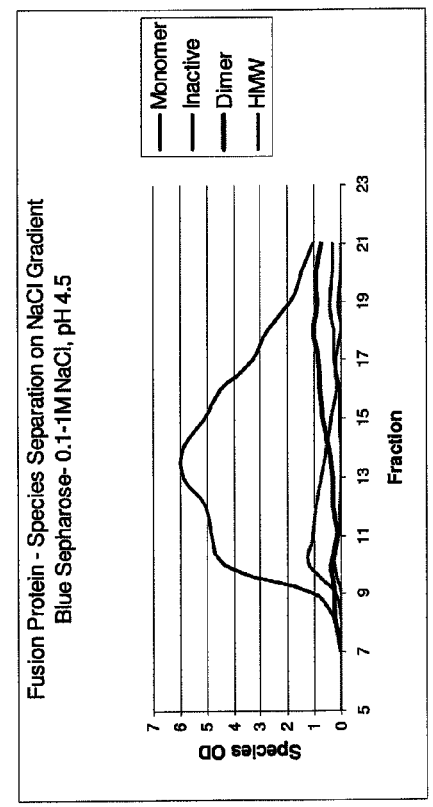
Fig. 2

Wash Experiments Attempting to Remove Inactive Species

- Use of cation exchange to reduce inactive forms of a fusion protein produced poor yield (55%)

- pH wash studies were done on Blue Sepharose targeting similar mechanism as cation exchange

- A 5 CV pH 6 wash, w/o NaCl removed inactive form but aggregate removal was still poor Capto™ Blue resin offered more opportunities for optimization to remove process-related impurities

| | % I-1 | % I-2 | % Active | % Active Yield |
|---|---|---|---|---|
| Fusion protein CM | 7.5 | 7.6 | 84.9 | -- |
| No PEG / 0.6M NaCl, pH 7 | 4.9 | 7.7 | 87.4 | 99.0 |
| 10% PEG w/ 0.6M NaCl, pH 7 | 1.8 | 6.8 | 91.4 | 99.0 |

I-1 and I-2 = inactive forms 1 and 2, respectively
pH wash with PEG addition to the elution removed mis-folded form
*"CM"=clarified media.

Fig. 4

PEG improved the removal of aggregates using both Blue Sepharose® and Capto™ Blue chromatography media

| | % HMW | % Mono. | % Mono. Yield |
|---|---|---|---|
| Fusion Protein CM | 29.1 | 68.6 | -- |
| Blue Sepharose 0.5M NaCl, pH 6 | 27.3 | 69.0 | 100 |
| .5M NaCl, pH 6 + 11% PEG | 5.6 | 93.5 | 88.5 |
| Capto Blue 0.6M NaCl, pH 7 | 23.1 | 74.0 | 98.6 |
| 0.6M NaCl, pH 7 + 10% PEG | 8.9 | 88.7 | 87.6 |

- 10-11% PEG substantially reduced aggregates and provided high monomer yield
- Nearly the same conditions gave comparable results between the 2 resins
- Capto Blue has higher binding capacity
- CM = clarified media; HMW = high molecular weight; LMW = low molecular weight

Fig. 5

PEG improved separation of aggregates from a mAb mixture using both Blue Sepharose® and Capto™ Blue

| | %HMW | %LMW | %Monomer | %Monomer Yield |
|---|---|---|---|---|
| mAb CM | 9.6 | 13.5 | 76.9 | -- |
| Blue Sepharose 0.4M NaCl, pH 7 | 12.2 | 5.2 | 82.6 | 95 |
| 0.4M NaCl, pH 7 + 7.5% PEG, | 1.0-2.0 | 5.2 | 93-94 | 85-90 |
| Capto Blue 0.55M NaCl, pH 8.5 | 3.4 | 5.2 | 91.4 | 95 |
| 0.55M NaCl, pH 8.5 + 2% PEG | 0.93 | 5.2 | 93.89 | 85-90 |

- 7.5% and 2% PEG addition in both Blue Sepharose and Capto Blue, respectively, resulted in a substantial reduction of aggregates with high monomer yield
- mAbs seem to require less PEG than fusion proteins

Fig. 7

PEG3350 can be removed using 30kDa diafiltration

- 10% PEG3350 in solution can be removed (>2 log10) after 5DV in 30 kDa UF/DF
- Alternatively, PEG can be removed by subsequent bind/elute chromatography (e.g. using anion exchange)

PEG enhanced viral clearance in blue resin chromatography purification procedures (fusion protein)

|  | X-MLV No PEG | X-MLV with PEG | MMV No PEG | MMV with PEG |
|---|---|---|---|---|
| Blue Sepharose FF | 1.3 - 1.4 | 5.2 | 0.4 | 2.0 - 2.2 |
| Capto Blue (high sub) | 2.2 | 4.9 | 1.4 | 3.0 |

- Viral clearance studies were carried out (duplicate expts) for 2 viruses under identical conditions except with or without PEG in the elution step
- Results show that addition of PEG in the elution step significantly increased viral clearance by
  - 1.5 $\log_{10}$ for MMV
  - 3.0 $\log_{10}$ for X-MLV

Fig. 10

Example Protocol for Improved Isolation of Antibodies Using Blue Sepharose® With PEG in the Elution Phase 1. EQ- 25mM Acetate, 300mM NaCl, pH 4.5
2. Load: Antibody CM adjusted to pH 4.5 (13mg titer/mL Resin)
3. Wash 1: 25mM Acetate, 300mM NaCl, pH 4.5
4. Wash 2: 25mM Acetate, pH 4.5
5. Wash 3: 25mM Bis TRIS, pH 6.0 *(NaCl <12.5mM NaCl)*

*Wash used to reduce/remove misfolded form*

6. Wash 4: 25mM Bis TRIS, 11%PEG, pH 6.0
7. Elution: 25mM Bis TRIS, 11%PEG, 0.5M NaCl, pH 6.0 (1+7CV)

*PEG present in elution buffer elute monomer while keeping aggregates bound to resin.*

8. Strip: 25mM Bis TRIS, 1M NaCl, pH 6.0
9. Regenerate: 0.5N NaOH

Fig. 11

Example of Results Obtained When Isolating Antibodies via Blue Sepharose® With PEG in the Elution Phase 1. EQ- 25mM Acetate, 300mM NaCl, pH 4.5
2. Load: Antibody CM adjusted to pH 4.5 (13mg titer/mL Resin)
3. Wash 1: 25mM Acetate, 300mM NaCl, pH 4.5
4. Wash 2: 25mM Acetate, pH 4.5
5. Wash 3: 25mM Bis TRIS, pH 6.0 *(NaCl <12.5mM NaCl)*
6. Wash 4: 25mM Bis TRIS, 11%PEG, pH 6.0
7. Elution: 25mM Bis TRIS, 11%PEG, 0.5M NaCl, pH 6.0 (1+7CV)
8. Strip: 25mM Bis TRIS, 1M NaCl, pH 6.0
9. Regenerate: 0.5N NaOH Dye-ligand affinity chromatography

SEQUENCE LISTING

```
<160> NUMBER OF SEQ ID NOS: 1

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325             330
```

PURIFICATION OF IMMUNOGLOBULINS

CROSS-REFERENCE TO RELATED APPLICATIONS

This application is the National Stage of International Application Number PCT/US2010/026219, filed Mar. 4, 2010, which claims the benefit of U.S. Provisional Application No. 61/157,850, fled Mar. 5, 2009, which is incorporated by reference herein.

REFERENCE TO A SEQUENCE LISTING SUBMITTED ELECTRONICALLY VIA EFS-WEB

The content of the electronically submitted sequence listing (Name: sequencelisting_ascii.txt; Size: 3,264 bytes; and Date of Creation: Sep. 2, 2011) is herein incorporated by reference in its entirety.

BACKGROUND OF THE INVENTION

The present invention pertains to improved methods of using dye-ligand affinity chromatography for the isolation or purification of antibodies or proteins containing an antibody fragment (such as Fc fusion proteins) from a mixture of undesirable contaminants (also known as PRIs or "product related impurities").

Monoclonal antibodies and Fc fusion proteins are being produced in cell culture in ever increasing quantities. With this comes the greater downstream challenge of maintaining sufficient resin capacity while being able to remove product-related impurities (PRIs; e.g., aggregates, half-antibodies, misfolded antibody forms). Traditional Protein-A purification processes employ a costly capture step to remove host cell proteins and DNA with little removal of PRIs, thus shifting the burden downstream to removal of PRIs (e.g., using HIC, SEC), often with substantial loss of yield. Removal of these PRIs can be the most challenging aspect of the purification process due to their higher starting quantities, their biochemical similarity to the product of interest, and their enrichment on Protein-A chromatography media. Alternative approaches to capture can be done at reduced cost but purity is often sacrificed. The ideal process thus would be a low cost capture step that delivers a product of high purity, yield and low PRI content.

Methods of using a low cost, non-traditional chromatography resin (a dye-ligand chromatography resin) was successfully developed for the capture of Fc-containing proteins at loading capacities comparable to Protein A resins. Optimizations of wash and elution steps with mobile phase modifiers resulted in significant removal of PRIs while maintaining high product purity and yield.

Dye-Ligand Affinity Chromatography

Dye-ligand affinity chromatography is a "mixed-mode" chromatographic media because such media rely on two separate forces to bind target molecules. In the case of dye-ligand affinity media these two forces are cation exchange and hydrophobic interactions. See FIG. 13.

For additional information on conventional methods in dye-ligand affinity chromatography there are numerous publications readily available and understood by those of ordinary skill in the art. See, for example:

Handbook of Affinity Chromatography by David S. Hage, $2^{nd}$ Edition, 2006, Chromatographic Science Series, vol. 92, Chapter 9, "Dye-Ligand and Biomimetic Affinity Chromatography" (CRC Press, 2006, ISBN 0824740572 and 9780824740573);

Dye-ligand chromatography for the resolution and purification of restriction endonucleases, Journal Applied Biochemistry and Biotechnology, Vol. 15, No. 3 (October, 1987), published by Humana Press Inc. (ISSN 0273-2289 (print) 1599-0291 (online);

Dye-ligand affinity chromatography: the interaction of Cibacron Blue F3GA with proteins and enzymes, by S. Subramanian S., CRC Crit Rev Biochem., 16(2): 169-205 (1984);

Affinity chromatography on immobilised triazine dyes-Studies on the interaction with multinucleotide-dependent enzymes, by Y. D. Clonis and C. R. Lowe CR., Biochim Biophys Acta., 659(1): 86-98 (1981);

Triazine-dye affinity; chromatography, by T. Atkinson, et al., Biochem Soc Trans., 9(4): 290-3 (1981);

The applications of reactive dyes in enzyme and protein downstream processing, Y. D. Clonis, Crit Rev Biotechnol, 7(4): 263-79 (1988);

Chromatography on immobilized reactive dyes, by E. Stellwagen, Methods Enzymol., 182: 343-57 (1990);

Dye-affinity techniques for bioprocessing: recent developments, N. Garg, et al., J Mol Recognit, 9(4): 259-74 (1996);

Dye-ligand affinity systems, by A. Denizli and E. Piskin, J Biochem Biophys Methods, 49(1-3): 391-416 (2001); and Well defined dye adsorbents for protein purification, J. Scoble and R. Scopes, J Mol Recognit, 9(5-6): 728-32 (1996).

Use of dye-ligand affinity chromatography for the purification of polypeptides such as antibodies and proteins containing antibody fragments (for example, Fc fusion proteins) is a desirable method of choice, if such media can be used efficiently and effectively, because dye-ligand affinity chromatography is relative inexpensive, is resistant to chemical and biological degradation, and is suitable for in situ cleaning and sterilization.

The potential utility of dye-ligands for protein purification was discovered in the 1960's when scientists found that the enzyme pyruvate kinase co-eluted with Blue Dextran during a column chromatographic purification procedure. Blue Dextran was, in turn, subsequently used to purify pyruvate kinase from human erythrocytes. See, Hage, page 232.

Since the 1960's dyes have been used as ligands for purification of proteins such as albumin and other blood proteins, oxidoreductases, decarboxylases, glycolytic enzymes, nucleases, hydrolases, lyases, synthases, and transferases. See, Hage, page 232.

Dye-ligand chromatographic media is available from a number of commercial sources such as Sigma-Aldrich Inc., Amersham Pharmacia Biotech Corp., BioRad Laboratories Inc., and GE Healthcare Biosciences Corp. Examples of such media include: BLUE-SEPHAROSE®, CAPTO™ BLUE, AFFI-GEL™ Blue Agarose, CB3GA-Agarose, Blue-Trisacryl, Reactive Brown 10-Sepharose, Reactive Green 19-Sepharose, Reactive Red 120-Sepharose, and Reactive Yellow 3-Sepharose. Additional examples of dye molecules which may be attached to insoluble chromatographic support matrices include Cibacron Blue 3GA, Procion Red HE-3B, Procione Rubine MX-B, Procion Yellow H-A, and Turqouise MX-G See, Hage, page 233.

Triazine dyes are the most common molecules use in dye-ligand chromatography. The chemical structure of such molecules typically comprise a chromophore unit (the color producing moiety) joined through an amino-bridge to another organic molecule (such as 1,3,5-sym-trichlorotriazine) used for attachment to an insoluble support (such as agarose, dextran, or cellulose).

BLUE-SEPHAROSE™ or, more particularly, BLUE SEPHAROSE™ 6 Fast Flow is an affinity chromatography medium commercially available from GE Healthcare Bio-Sciences Corp. (Piscataway, N.J.). BLUE SEPHAROSE™ 6 Fast Flow is a chromatography medium comprising a bead structure of 6% highly cross-linked agarose to which Cibacron Blue 3G dye has been covalently linked at a density of approximately 7 micromols Cibacron Blue 3G 3G/mL of drained medium. GE Healthcare reports that "BLUE SEPHAROSE™ 6 Fast Flow is Cibacron Blue 3G covalently attached to the SEPHAROSE™ 6 Fast Flow "matrix by the triazine coupling method. The blue dye binds many proteins, such as albumin, interferon, lipoproteins and blood coagulation factors. It also binds several enzymes including kinases, dehydrogenases, and most enzymes requiring adenyl-containing cofactors e.g. NAD+. The highly cross-linked matrix provides a stable, rigid medium. Blue Sepharose Fast Flow belongs to the BIOPROCESS™ media family. BIOPROCESS™ media are separation media developed, made and supported for industrial scale—especially the manufacture of healthcare products. With their high physical and chemical stability, very high batch-to-batch reproducibility, and Regulatory Support File back-up, BioProcess media are ideal for all stages of an operation—from process development through scale-up and into production." See, GE Healthcare Bio-Sciences Literature File No. 71-7055-00 AG (printed in Sweden by Wikströms, Uppsala, January 2006 (No. 1050991)); this literature file is hereby incorporated by reference solely to the extent that it does not contradict or conflict with the teachings in the present patent application; in the event that contradictions or conflicts exist, the present application is intended to supercede and/or take precedence over any such contradictory or conflicting material.

CAPTO™ BLUE is an affinity chromatography medium commercially available from GE Healthcare Bio-Sciences Corp. (Piscataway, N.J.). CAPTO™ BLUE is a chromatography medium comprising a bead structure of highly cross-linked agarose to which Cibacron Blue dye has been covalently linked at a density of approximately 11 to 16 micromols Cibacron/mL of medium. GE Healthcare markets CAPTO™ BLUE "for the capture of albumin, as well as purification of enzymes and recombinant proteins at laboratory and process scale." GE Healthcare also reports that CAPTO™ BLUE was "[d]eveloped from Blue Sepharose™ 6 Fast Flow, [and] Capto Blue is more chemically stable and has a more rigid agarose base matrix than its predecessor. These improvements allow the use of faster flow rates and larger sample volumes, leading to higher throughput with no significant reduction in binding capacity." See, GE Healthcare Bio-Sciences Data File No. 28-9392-46 AA (06/2008); this data file is hereby incorporated by reference solely to the extent that it does not contradict or conflict with the teachings in the present patent application; in the event that contradictions or conflicts exist, the present application is intended to supercede and/or take precedence over any such contradictory or conflicting material.

Optimal conditions for isolating a protein using a dye-ligand chromatography media are determined empirically depending on the specific target protein to be isolated. Variables likely to have significant effect on the ability to efficiently and effectively isolate or purify a protein include: pH; ionic strength of the solution; the composition of the mixture which the protein is in; temperature, sample size; and, of course, the specific dye-ligand and support matrix being used.

Purification of Antibodies Using Protein-A and Other Procedures

Protein-A affinity chromatography is one of the most widely used methods for the capture and isolation of monoclonal antibodies (mAbs) and Fc-fusion proteins. Protein-A is quite effective in removing host cell protein (HCP) and DNA while producing antibody mixtures of relatively high yield. Disadvantages to use of protein-A, however, include the binding and co-elution of PRIs with the target antibody, co-elution of aggregates, mis-folded antibody forms, and half-antibodies. Thereafter, following protein-A purification there is often considerable loss of antibody yield resulting from subsequent procedures (e.g., ion exchange and hydrophobic interaction chromatography methods) aimed at removing PRIs.

Other separation methods have also been routinely employed for the purification of antibodies. Such methods commonly rely on interactions based on charge (e.g., ion exchange), hydrophobicity (HIC; hydrophobic interaction chromatography), size (e.g., size exclusion chromatography), affinity (as with Protein-A) or combinations of such methods.

A patent application by Gagnon teaches use of PEG (or other aqueous soluble nonionic organic polymers) in mixed-mode chromatography antibody purification procedures. See, U.S. Patent Application Pub. No. 2008/0177048, filed Jan. 7, 2008, published Jul. 24, 2008 (hereinafter "Gagnon"). An important distinction of the present invention over Gagnon, however, is that Gagnon teaches that use of PEG enhances the binding capacity of antibodies, aggregates, and viruses on the various types of mixed-mode chromatography resins listed therein. In particular, Gagnon emphasizes the use of PEG throughout the chromatography purification steps as a means of enhancing the resin binding capacity (i.e., incorporation of PEG when antibody is first applied to the column and use of PEG in the wash and elution phases). Indeed, Gagnon teaches that "the presence of nonionic organic polymer preferentially enhances the retention of antibody on mixed mode chromatography supports in comparison to most contaminating proteins . . . " See e.g., Gagnon at page 2, paragraph [0014] (emphasis added). Although Gagnon lists multiple types of available mixed mode chromatographic resins and types of interaction forces (see e.g., Gagnon paragraph [0003] and [0012]), the clear emphasis in Gagnon is on, and all of the examples were done with, hydroxyapatite chromatography resins. More particularly, Gagnon does not include any mention of dye-ligand chromatography resins, in general, or blue-dye chromatography resins, in particular. Moreover, in contrast to the "enhanced retention" of antibodies on mixed-mode resins in the presence of organic polymers taught in Gagnon, the present invention pertains to use of organic polymers (such as PEG) to specifically elute target antibodies from dye-ligand chromatography resins by incorporating organic polymers (such as PEG) only in the elution phase (such as in a single-step or gradient-elution phase). In other words, with dye-ligand chromatography resins, organic polymers such as PEG are not used to enhance binding of antibodies to the resin, but are instead used to elute target antibodies from the resin. Indeed, this distinction may explain the comment in Gagnon that "Mixed mode chromatography supports provide unique selectivities that cannot be reproduced by single mode chromatography methods such as ion exchange, however method development is complicated, unpredictable, and may require extensive resources. Even then, development of useful procedures may require long periods of time, as exemplified by hydroxyapatite." See, Gagnon, paragraph [0004].

BRIEF SUMMARY OF THE INVENTION

The present invention pertains to improved methods of using dye-ligand affinity chromatography for the isolation or purification of antibodies or proteins comprising an antibody fragment (such as Fc fusion proteins) from a mixture of undesirable contaminants. (For purposes of simplicity, unless stated otherwise, the term "antibody" or "antibodies" as used anywhere herein, including the Figures and Claims is intended to include antibodies as these polypeptides are commonly understood in the art and also to include proteins comprising a portion of an antibody, such as Fc fusion proteins).

It has now been discovered that use of an organic polymer such as polyethylene glycol (PEG) in the elution phase of an antibody/dye-ligand affinity chromatography isolation procedure results in enhanced (improved) separation of the target antibody from contaminants initially in the antibody mixture (compared to the same procedure when elution is performed in the absence of an organic polymer such as PEG). In one embodiment, the methods described herein are particularly useful in separating or removing antibody aggregates, misfolded antibodies, and virus contaminants from the target antibody. Misfolded antibodies may be distinguished from antibody aggregates by the lower molecular mass of the former compared to the latter. Misfolded antibodies may be distinguished from properly folded antibodies of the same molecular mass by the biological inactivity of the former compared to the latter.

BRIEF DESCRIPTION OF THE DRAWINGS/FIGURES

FIG. 1: Binding capacity study comparing binding of an Fc-fusion protein on Blue SEPHAROSE® versus CAPTO™ BLUE.

FIG. 2: NaCl gradient elution experiments showed poor resolution of aggregates and inactive forms.

Figure 3:
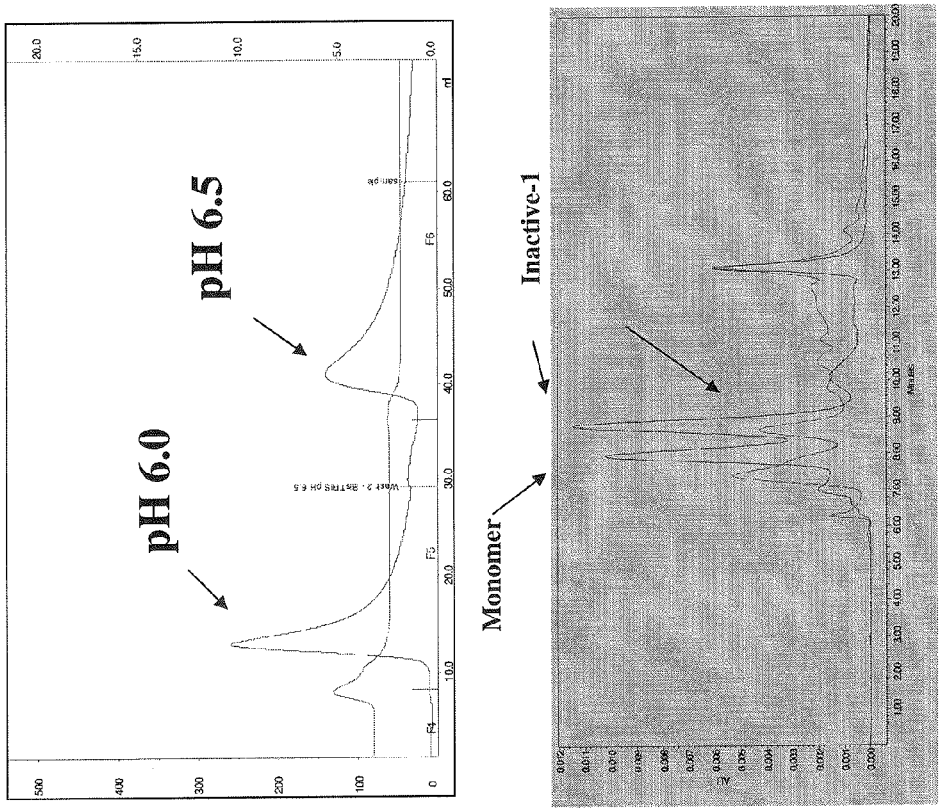

FIG. 3: Wash experiments attempting to remove inactive species.

FIG. 4: CAPTO™ BLUE resin offered more opportunities for optimization to remove process-related impurities.

FIG. 5: PEG improved the removal of aggregates using both Blue Sepharose® and CAPTO™ BLUE chromatography media.

Figure 6:
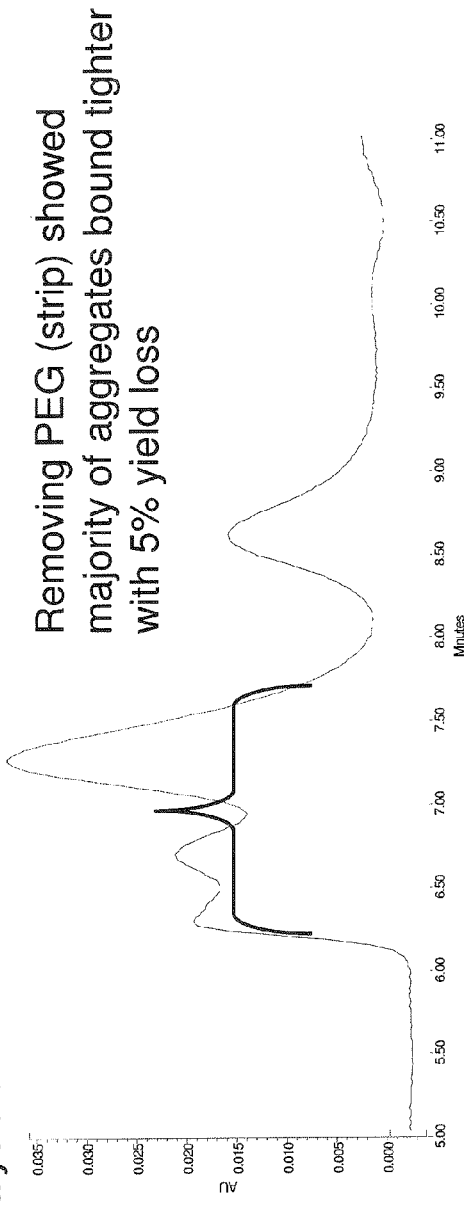

FIG. 6: PEG improved the separation of aggregates from a fusion protein.

FIG. 7: PEG improved separation of aggregates from a mAb mixture using both BLUE SEPHAROSE® and CAPTO™ BLUE.

Figure 8:
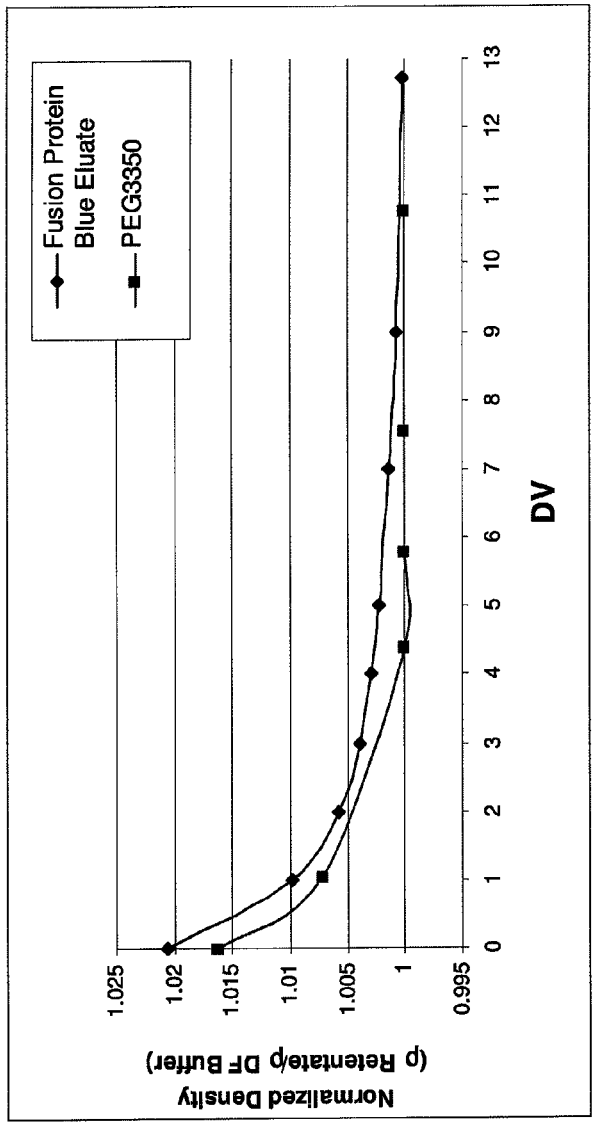

FIG. 8: PEG-3350 can be removed using 30 1cDa diafiltration.

Figure 9:
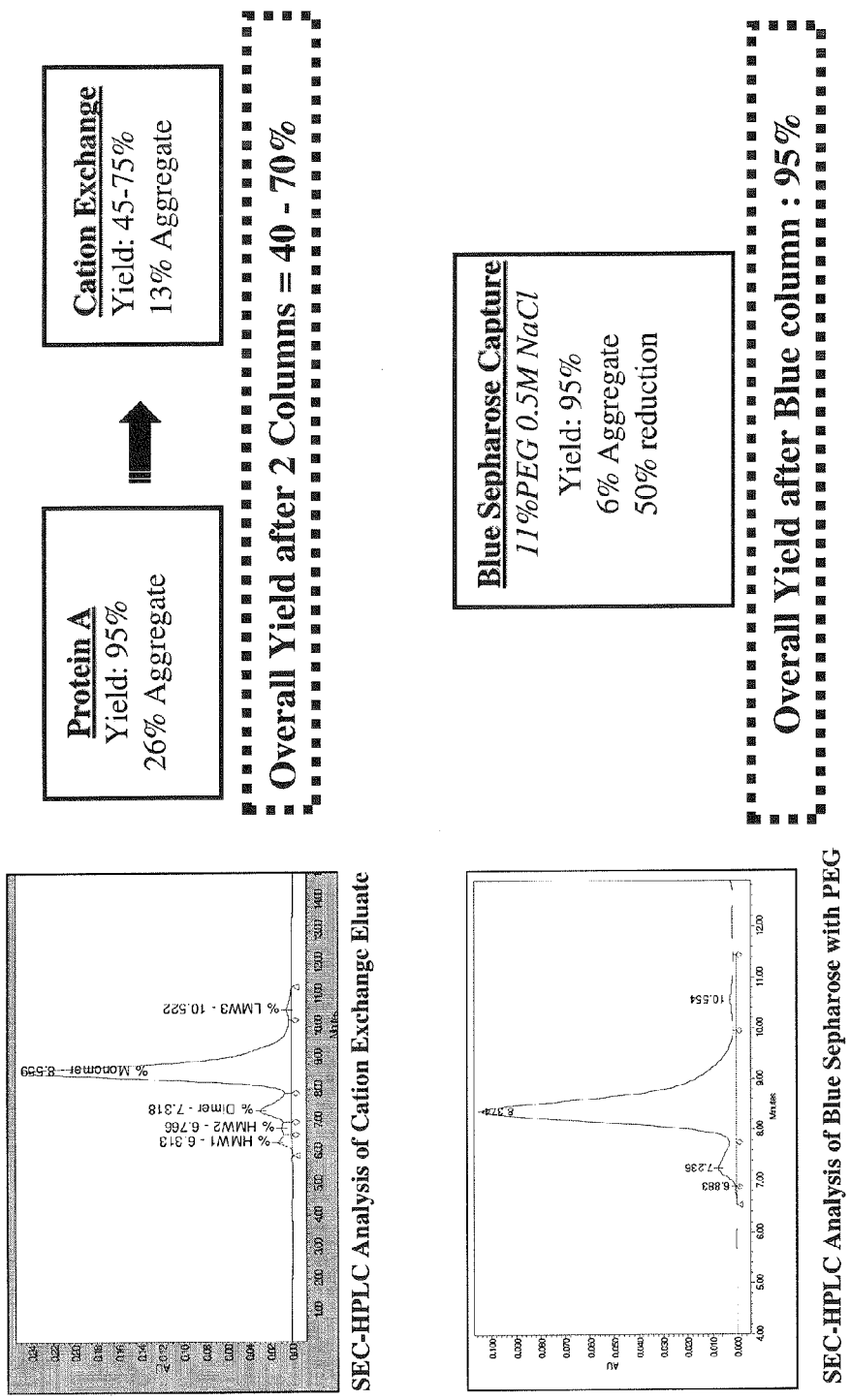

FIG. 9: BLUE SEPHAROSE® provided superior yield and purity compared to Protein A/Ion Exchange purification procedures.

FIG. 10: PEG enhanced viral clearance in blue resin chromatography purification procedures.

FIG. 11: Example protocol for improved isolation of antibodies using BLUE SEPHAROSE® with PEG in the elution Phase.

Figure 12:
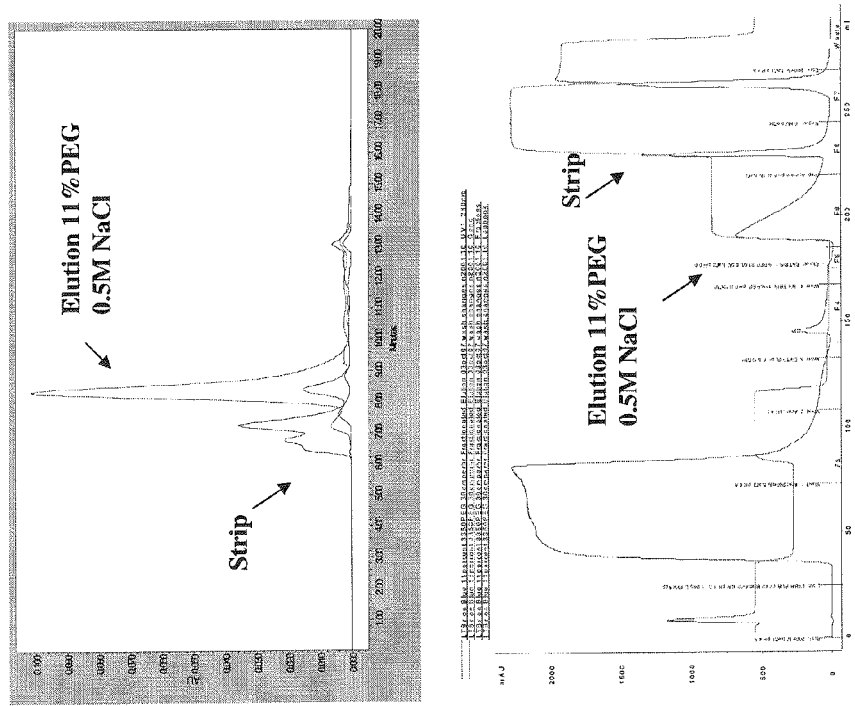

FIG. 12: Example of results obtained when isolating antibodies via BLUE SEPHAROSE® with PEG in the elution phase.

Figure 13:
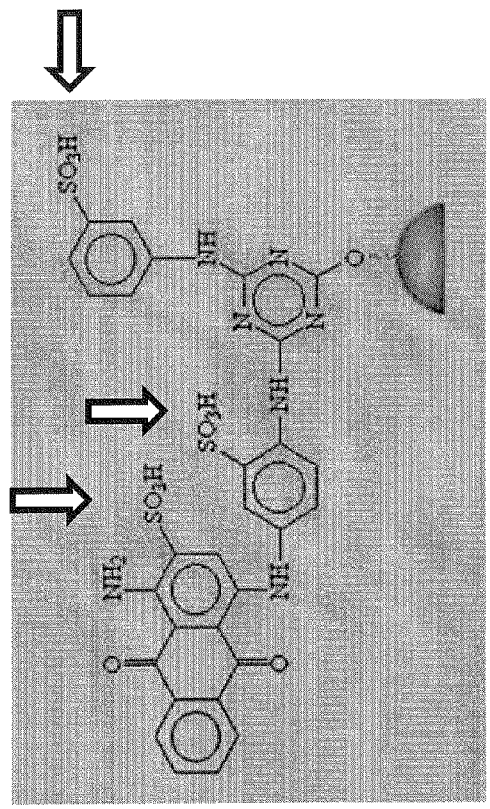

FIG. 13: Example dye-ligand affinity chromatography moiety.

DETAILED DESCRIPTION OF THE INVENTION

Development of the present invention was motivated by a desire to implement a relatively inexpensive but rapidly and efficient means of purifying antibodies and Fc fusion proteins. In particular, the effects of mobile phase modifiers (such as PEG) in dye-affinity chromatographic isolation procedures were investigated. It was discovered that the use of an organic polymer (such as PEG) during the elution phase of dye-ligand chromatography purification procedures provided enhanced clearance (purification) of target antibodies from PRIs such as viruses, misfolded antibodies, and antibody aggregates.

As used herein, "organic polymer" refers to an aqueous-soluble uncharged linear, branched, or otherwise structured polymer of organic composition. Examples include, but are not limited to ethylene glycol, polyethylene glycol, and polypropylene glycol. Examples include, but are not limited to, compositions with an average polymer molecular weight ranging from 100 to 20,000 daltons. The average molecular weight of commercial PEG preparations are typically indicated by a hyphenated suffix. For example, PEG-3500 refers to a preparation with an average molecular weight of about 3,500 daltons.

PEG is an uncharged organic polymer that is "preferentially excluded" from protein surfaces by virtue of it hydrophilicity. The presence of PEG causes proteins to share a "water shell" wherein proteins (such as antibodies) are surrounded or coated by at least one molecular layer of water molecules. This condition, however, creates a thermodynamically unfavorable condition. Thus, in the presence of PEG, antibodies and other molecules or contaminants more strongly "seek" or have an increased attraction for a more favorable theromdynamic condition, such as may be found by association with a dye-ligand affinity matrix.

Some other advantages of PEG are that it is inexpensive and available in a variety of molecular weights (MW). It exists in a liquid form if the MW is <1000 Da and it is in a powder form if >1000 Da. The available variety of differing MW PEGs allows for selectivity in combining optimal size PEG molecules based on differing MWs and pI (isoelectric points) of target proteins and antibodies.

As described herein, one embodiment of the present invention resulted from discovery that inclusion of PEG in an antibody purification procedure using BLUE SEPHAROSE® chromatography produced the successful capture (isolation) and improved removal of aggregates from an initial mixture containing the target antibody. Indeed, the addition of PEG to the elution buffer resulted in highly selective elution of antibody monomer while maintaining aggregates bound tightly to the resin.

Additionally, non-ionic aqueous soluble organic polymers similar to PEG which may also be used in like manner as PEG for the isolation or purification of antibodies on dye-ligand chromatography media include, but are not limited to, ethylene glycol, polyethylene glycol, and polypropylene glycol.

Ethylene Glycol

Ethylene glycol (monoethylene glycol (MEG), 1,2-ethanediol) is an alcohol with two "OH" groups (i.e., a diol). In its pure form, it is an odorless, colorless, sweet-tasting, toxic liquid. Ethylene glycol is produced from ethylene, via the intermediate ethylene oxide. Ethylene oxide reacts with water to produce ethylene glycol according to the chemical equation:

$$C_2H_4O + H_2O \rightarrow HO-CH_2-CH_2-OH$$

This reaction can be catalyzed by either acids or bases, or can occur at neutral pH under elevated temperatures. The major byproducts are the ethylene glycol production are the oligomers diethylene glycol, triethylene glycol, and tetraethylene glycol. An embodiment of the present invention includes use of any available forms of ethylene glycol in the isolation (purification) of antibodies.

Polyethylene Glycol (PEG)

Polyethylene glycol (PEG), also known as polyethylene oxide (PEO) or polyoxyethylene (POE), is an organic polymer (in particular, a type of polyether because it is a polymer of ethylene oxide). PEGs are prepared by polymerization of ethylene oxide and are commercially available over a wide range of molecular weights from 300 g/mol to 10,000,000 g/mol with the following structure:

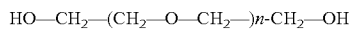

HO—CH$_2$—(CH$_2$—O—CH$_2$—)$n$-CH$_2$—OH (Where "n" is any number giving rise to a molecular weight from 300 g/mol to 10,000,000 g/mol.)

Most PEG compositions include molecules with a distribution of molecular weights instead of a single uniform molecular weight. The size distribution can be characterized statistically by its average molecular weight (MW). PEGs are also available with different geometries. Branched PEGs generally have 3 to 10 PEG chains emanating from a central core group. "Star" PEGs generally have 10-100 PEG chains emanating from a central core group. "Comb" PEGs have multiple PEG chains normally grafted to a polymer backbone. An embodiment of the present invention includes use of any available forms of PEG in the isolation (purification) of antibodies.

Polypropylene Glycol (PPG)

Polypropylene glycol or polypropylene oxide is the polymer of propylene glycol (long chain polymers attached to a glycerine backbone). Polypropylene glycol is a polyether. The term polypropylene glycol or PPG is reserved for low to medium range molecular weight polymer when the nature of the end-group, which is usually a hydroxyl group, has a significant bearing on the total molecular weight of the molecule. The term "oxide" is used for high range molecular weight polymer when end-groups no longer affect polymer properties. PPG has many properties in common with polyethylene glycol. The polymer is a liquid at room temperature. Solubility in water decreases rapidly with increasing molar mass. Most PPG compositions include molecules with a distribution of molecular weights instead of a single uniform molecular weight. The size distribution can be characterized statistically by its average molecular weight (Mw).

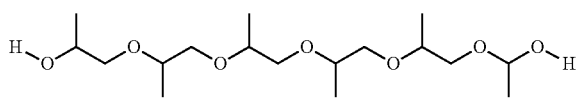 [SMILES: CC(O)COC(C)COC(C)COC(C)COC(C)COC(C)O]

An embodiment of the present invention includes use of any available forms of PPG in the isolation (purification) of antibodies.

Contaminants or Product Related Impurities

"Contaminants" or product related impurities (PRIs) as used herein refers to any molecule or compound which is preferably or desirably removed or separated from the target molecule. (For purposes of the present invention the target molecule is an antibody or protein containing an antibody fragment, such as an Fc fusion protein). Examples of contaminants or PRIs include, but are not limited to, viruses, host cell proteins, misfolded proteins, aggregated proteins, half-antibodies, protein dimers, nucleic acids such as DNA or RNA, and endotoxins.

Examples of Chromatographic Media and Dyes

Examples of dye-ligand chromatographic media that may be used for purification of antibodies in conjunction with organic polymers include, but are not limited to:
CAPTO™ BLUE;
BLUE-SEPHAROSE®;
AFFI-GEL BLUE™ agarose;
CB3GA-Agarose;
Blue-Trisacryl;
Reactive Brown 10-Sepharose;
Reactive Green 19-Sepharose;
Reactive Red 120-Sepharose;
Reactive Yellow 3-Sepharose.

*AFFI-GEL BLUE™ agarose is a cross-linked agarose bead with covalently attached Cibacron Blue F3GA dye; this medium is commercially available from BioRad Laboratories (Hercules, Calif., USA).

Examples of dyes that may be used in conjunction with a chromatographic media for purification of antibodies (in conjunction with organic polymers) include, but are not limited to:
Cibacron Blue;
Reactive Blue 2;
Blue-B;
Blue Dextran;
Procion Red HE-3B;
Procione Rubine MX-B;
Procion Yellow H-A;
Turqouise MX-G Antibodies The terms "antibody" and "immunoglobulin" (or plural forms thereof) may used interchangeably herein. Basic immunoglobulin structures in vertebrate systems are relatively well understood. See, e.g., Harlow et al., Antibodies: A Laboratory Manual, (Cold Spring Harbor Laboratory Press, 2nd ed. 1988). The term "antibody" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan and, accordingly, are within the scope of the instant invention.

Antibodies and antibody fragments include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to IGF-1R antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibodies or antibody fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

Fc Fusion Proteins

As used herein, unless stated otherwise, the term "Fc fusion protein" is intended to include proteins that have, contain, or comprise an immunoglobulin Fc region. Fc fusion proteins, which can be recombinant or naturally occurring, include an Fc region or a region equivalent to the Fc region of an immunoglobulin. An example of an Fc-containing protein is one such as an enzymatically-active Factor VIII:Fc fusion protein. Fc fusion proteins do not need to be enzymatically active for isolation or purification according to the methods of the present invention.

As used herein, the term "Fc region" is intended to refer to a C-terminal region of an IgG heavy chain. In one embodiment, the Fc region refers to the C-terminal region of a human IgG heavy chain (see, e.g., SEQ ID NO.: 1). Although the boundaries of the Fc region of an IgG heavy chain might vary slightly, the human IgG heavy chain Fc region is usually defined to span from the amino acid residue at position $Cys^{226}$ of the native polypeptide (or $Cys^{109}$ of SEQ ID NO.: 1) to the carboxyl-terminus.

As used herein, the term region equivalent to the Fc region of an immunoglobulin" is intended to include naturally occurring allelic variants of the Fc region of an immunoglobulin as well as genetically or artificially engineered variants having alterations which produce substitutions, additions, or deletions. For example, one or more amino acids can be deleted from the N-terminus or C-terminus of the Fc region of an immunoglobulin without substantial loss of function. Likewise, one or more amino acids can be inserted, deleted, or substituted within the Fc region without substantial loss of function. Such variants can be made according to biochemical principles known in the art so as to have minimal effect on activity or efficiency of isolation via dye-ligand chromatography media.

As used herein, the terms "fusion" and "chimeric," when used in reference to polypeptides such as an Fc fusion protein, refer to polypeptides comprising amino acid sequences derived from two or more heterologous polypeptides, such as portions of proteins encoded by separate genes (whether said genes occur in the same or a different species of organism).

As used herein, the term "variant" (or analog) refers to a polypeptide differing from a specifically recited polypeptide of the invention, such as FcRn, by amino acid insertions, deletions, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous peptides, e.g., human, primate, mouse, rat, bovine, porcine, and minimizing the number of amino acid sequence changes made in regions of high homology (conserved regions) or by replacing amino acids with consensus sequences.

As used herein the term "native" (or naturally-occurring) polypeptide refers to an amino acid sequence that is identical to an amino acid sequence of an Fc region commonly found in nature. For example, native sequence human Fc regions include a native sequence human IgG1 Fc region (non-A and A allotypes); native sequence human IgG2 Fc region; native sequence human IgG3 Fc region; and native sequence human IgG4 Fc region, as well as, naturally occurring variants thereof. Other sequences are contemplated and are readily obtained from various databases (e.g., the National Center for Biotechnology Information (NCBI)).

EXAMPLES

Some parameters to be considered in empirically establishing optimal conditions for the isolation of particular antibodies during dye-ligand chromatography procedures include, but are not limited to, a determination of the optimal pH, ionic strength of starting samples, washes, and eluates (e.g., sodium chloride concentration), and concentration and MW of PEG or other organic polymer to be used.

Specific examples of experiments performed are shown and described in the Figures presented herein. Conclusions determined as a result of these experiments include, without limitation, the discovery that the incorporation of organic polymers, such as PEG, as part of the elution step in dye-ligand chromatography separation procedures provides the ability to successfully, effectively, and efficiently:

Isolate (purify) antibodies and Fc containing proteins from complex mixtures of solutions containing numerous contaminants (e.g., isolation of antibodies from clarified cell media harvested from recombinant cell cultures);

Remove product-related impurities while providing a high yield of target protein;

Remove mis-folded antibody forms;

Improve resolution and clearance of antibody aggregates;

Significantly enhance virus clearance; and,

Provide a purification process with 4-6 fold lower cost than Protein A procedures.

CAPTO™ BLUE resin offered more opportunities for optimization to remove process-related impurities as shown in Table 1 and FIG. 4.

TABLE 1

|  | % I-1 | % I-2 | % Active | % Active Yield |
|---|---|---|---|---|
| Fusion protein CM | 7.5 | 7.6 | 84.9 | — |
| No PEG/0.6M NaCl, pH 7 | 4.9 | 7.7 | 87.4 | 99.0 |
| 10% PEG w/ 0.6M NaCl, pH 7 | 1.8 | 6.8 | 91.4 | 99.0 |

In Table 1, I-1 and 1-2=inactive forms 1 and 2, respectively. A pH wash with PEG addition to the elution removed mis-folded form. "CM" is clarified media.

PEG improved the removal of aggregates using both BLUE SEPHAROSE® and CAPTO™ BLUE chromatography media as shown in Table 2 and FIG. 5.

TABLE 2

|  | % HMW | % Mono. | % Mono. Yield |
|---|---|---|---|
| Fusion Protein CM | 29.1 | 68.6 | — |
| BLUE SEPHAROSE ® |  |  |  |
| 0.5M NaCl, pH 6 | 27.3 | 69.0 | 100 |
| .5M NaCl, pH 6 + 11% PEG | 5.6 | 93.5 | 88.5 |
| CAPTO ™ BLUE |  |  |  |
| 0.6M NaCl, pH 7 | 23.1 | 74.0 | 98.6 |
| 0.6M NaCl, pH 7 + 10% PEG | 8.9 | 88.7 | 87.6 |

In Table 2, 10-11% PEG substantially reduced aggregates and provided higher monomer yield. Nearly the same conditions gave comparable results between the two resins. CAPTO™ BLUE has higher binding capacity. "HMW" is high molecular weight.

PEG improved separation of aggregates from a mAb mixture using both BLUE SEPHAROSE® and CAPTO™ BLUE as shown in Table 3 and FIG. 7.

TABLE 3

|  | % HMW | % LMW | % Monomer | % Monomer Yield |
|---|---|---|---|---|
| mAb CM | 9.6 | 13.5 | 76.9 | — |
| BLUE SEPHAROSE® |  |  |  |  |
| 0.4M NaCl, pH 7 | 12.2 | 5.2 | 82.6 | 95 |
| 0.4M NaCl, pH 7 + 7.5% PEG | 1.0-2.0 | 5.2 | 93-94 | 85-90 |
| CAPTO™ BLUE |  |  |  |  |
| 0.55M NaCl, pH 8.5 | 3.4 | 5.2 | 91.4 | 95 |
| 0.55M NaCl, pH 8.5 + 2% PEG | 0.93 | 5.2 | 93.89 | 85-90 |

As shown in Table 3 and FIG. 7, 7.5% and 2% PEG addition in both BLUE SEPHAROSE® and CAPTO™ BLUE, respectively, resulted in a substantial reduction of aggregates with high monomer yield. mAbs seem to require less PEG than fusion proteins.

PEG enhanced viral clearance in blue resin chromatography purification procedures (fusion protein) as shown in Table 4 and FIG. 10.

TABLE 4

|  | X-MLV No PEG | X-MLV with PEG | MMV No PEG | MMV with PEG |
|---|---|---|---|---|
| BLUE SEPHAROSE® FF | 1.3-1.4 | 5.2 | 0.4 | 2.0-2.2 |
| CAPTO™ BLUE (high sub) | 2.2 | 4.9 | 1.4 | 3.0 |

As shown in Table 4 and FIG. 10, viral clearance studies were carried out (duplicate experiments) for two viruses under identical conditions except with or without PEG in the elution step. Results show that addition of PEG in the elution step significantly increased viral clearance by 1.5 $\log_{10}$ for MMV and 3.0 $\log_{10}$ for X-MLV. See Table 4 and FIG. 10.

An example protocol for improved isolation of antibodies using BLUE SEPHAROSE® with PEG in the elution Phase is:

(1) Equilibate (EQ) chromatography column witn 25 mM Acetate, 300 mM NaCl, pH 4.5;

(2) Load: Antibody CM adjusted to pH 4.5 (13 mg titer/mL resin);

(3) Wash 1: 25 mM Acetate, 300 mM NaCl, pH 4.5;

(4) Wash 2: 25 mM Acetate, pH 4.5;

(5) Wash 3: 25 mM Bis TRIS, pH 6.0 (NaCl<12.5 mM NaCl)

Note: Wash used to reduce/remove misfolded form (6) Wash 4: 25 mM Bis TRIS, 11% PEG, pH 6.0;

(7) Elute: 25 mM Bis TRIS, 11% PEG*, 0.5M NaCl, pH 6.0 (1+7CV)

Note: PEG in elution buffer elutes antibody monomer while keeping aggregates bound to resin;

(8) Strip column clean: 25 mM Bis TRIS, 1M NaCl, pH 6.0;

(9) Regenerate column: 0.5N NaOH;

(10) Pool, quantitate, measure bioactiviy, or otherwise characterize target antibodies collected in the eluate fractions.

Note: Experimental results indicate that isolation of monoclonal antibodies appears to require lower concentrations of PEG compared to isolation of Fc fusion proteins. Compare, for example, Table 2 and FIG. 5 (Fc fusion protein eluted with 10-11% PEG) versus Table 3 and FIG. 7 (Mab eluted with 2% (CAPTO™ BLUE) and 7.5% PEG (BLUE SEPHAROSE®)).

It is to be appreciated that the Detailed Description section, and not the Abstract, is intended to be used to interpret the claims. The Abstract may set forth one or more but not all exemplary embodiments of the present invention as contemplated by the inventor(s), and thus, is not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, chromatography conditions, and so forth used in the specification, figures, and claims are to be understood as being modified in all instances by the term "about." Accordingly, unless indicated to the contrary, the numerical parameters set forth in the specification, figures, and claims are approximations that may vary depending upon the desired performance sought to be obtained by the present invention.

The breadth and scope of the present invention should not be limited by any of the above-described exemplary embodiments, but should be defined only in accordance with the following claims and their equivalents.

Additional References

P. Ganon, "Nonionic polymer enhancement of aggregate removal in Ion Exchange and Hydroxyapatite chromatography." Presentation at 12th Annual Waterside Conference, San Juan, Puerto Rico (Apr. 23-25, 2007).

Gagnon, P., 2009, Purification of Monoclonal Antibodies by Mixed-Mode Chromatography, in. Process Scale Purification of Antibodies, Gottschalk, U., ed., pp. 125-144, John Wiley and Sons, New York, ISBN 978-0-470-20962-2.

Gagnon, P., 2008, The Emerging Generation of Chromatography Tools for Virus Purification, BioProcess International, Vol. 6, Sup. 6, 24-30.

P. Gagnon, 1996, Purification Tools for Monoclonal Antibodies, Validated Biosystems, Tucson, ISBN 0-9653515-9-9 (1996).

Gagnon et al., "A method for obtaining unique selectivities in ion exchange chromatography by adding organic solvents to the mobile phase," Poster and Oral presentation, 15th International Symposium on HPLC of Proteins, Peptides, and Polynucleotides, Boston (1995).

What is claimed is:

1. A method of separating an antibody or a protein comprising an antibody fragment from one or more contaminants wherein said method comprises:
   a) contacting said antibody or protein and said one or more contaminants with a dye-ligand chromatography media;
   b) contacting said dye-ligand chromatography media with an organic polymer; and
   c) after steps a) and b), removing said antibody or said protein from contact with said dye-ligand chromatography media,
   wherein the molecular weight of the organic polymer is from 100 dalton to about 20,000 dalton; and
   wherein contacting the dye-ligand chromatography media with the organic polymer according to step b) enhances separation of the antibody or protein from the one or more contaminants as compared to separation of the antibody or protein from the one or more contaminants without contacting the dye-ligand chromatography media with the organic polymer according to step b).

2. The method of claim 1 wherein steps a) and b) are performed simultaneously.

3. The method of claim 1 wherein step a) is performed before step b).

4. The method of claim 1 wherein step a) is performed after step b).

5. The method of claim 1 wherein said organic polymer is polyethylene glycol (PEG).

6. The method of claim 1 wherein said organic polymer is polypropylene glycol or polypropylene oxide.

7. The method of claim 1 wherein said dye-ligand chromatography media comprises a triazine dye-ligand.

8. The method of claim 1 wherein said dye-ligand chromatography media comprises a blue dye-ligand.

9. The method of claim 1 wherein said dye-ligand chromatography media comprises a dye selected from the group consisting of:
   a) Cibacron Blue;
   b) Reactive Blue 2;
   c) Blue-B;
   d) Blue Dextran;
   e) Procion Red HE-3B;
   f) Procione Rubine MX-B;
   g) Procion Yellow H-A; and
   h) Turqouise MX-G.

10. The method of claim 1 wherein said dye-ligand chromatography media is selected from the group consisting of:
   a) CAPTO™ BLUE;
   b) BLUE-SEPHAROSE®;
   c) AFFI-GEL BLUE SEPHAROSE®;
   d) CB3GA-Agarose;
   e) Blue-Trisacryl;
   f) Reactive Brown 10-Sepharose;
   g) Reactive Green 19-Sepharose;
   h) Reactive Red 120-Sepharose; and
   i) Reactive Yellow 3-Sepharose.

11. The method of claim 1 wherein said antibody or protein comprising an antibody fragment is eluted from said chromatography media in the absence of a portion of said one or more contaminants initially associated with said antibody or protein.

12. The method of claim 1 wherein said antibody or protein comprising an antibody fragment is separated from a portion of said one or more contaminants initially associated with said antibody or protein, wherein said contaminants are selected from the group consisting of:
   a) misfolded antibodies or misfolded proteins comprising an antibody fragment;
   b) aggregated antibodies or aggregated proteins comprising an antibody fragment;
   c) half-antibodies;
   d) protein dimers;
   e) a virus or virion proteins;
   f) host cell protein;
   g) endotoxin; and
   h) nucleic acid.

13. The method of claim 11 wherein said portion of said one or more contaminants separated from said antibody or protein is a fraction selected from the group consisting of:
   a) about 50% or more of said one or more contaminants;
   b) about 60% or more of said one or more contaminants;
   c) about 70% or more of said one or more contaminants;
   d) about 75% or more of said one or more contaminants;
   e) about 80% or more of said one or more contaminants;
   f) about 85% or more of said one or more contaminants;
   g) about 90% or more of said one or more contaminants;
   h) about 95% or more of said one or more contaminants;
   i) about 96% or more of said one or more contaminants;
   j) about 97% or more of said one or more contaminants;
   k) about 98% or more of said one or more contaminants;
   l) about 99% or more of said one or more contaminants; and
   m) about 100% of said one or more contaminants.

14. The method of claim 1 wherein the antibody fragment of said protein comprising an antibody fragment is an antibody Fc region or an antibody Fc domain.

15. The method of claim 1 wherein said protein comprising an antibody fragment is a fusion protein.

16. The method of claim 1 wherein said chromatography media is contacted with PEG at a final weight-to-volume concentration selected from the group consisting of:
   a) about 0.1 to about 50% PEG;
   b) about 0.1 to about 40% PEG;
   c) about 0.1 to about 30% PEG;
   d) about 0.1 to about 20% PEG;
   e) about 0.1 to about 10% PEG;
   f) about 0.1 to about 5% PEG;
   g) about 0.1 to about 2% PEG;
   h) about 1 to about 50% PEG;
   i) about 1 to about 40% PEG;
   j) about 1 to about 30% PEG;
   k) about 1 to about 20% PEG;
   l) about 1 to about 10% PEG;

m) about 1 to about 5% PEG;
n) about 1 to about 2% PEG;
o) about 2 to about 50% PEG;
p) about 2 to about 40% PEG;
q) about 2 to about 30% PEG;
r) about 2 to about 20% PEG;
s) about 2 to about 10% PEG;
t) about 2 to about 5% PEG;
u) about 5 to about 50% PEG;
v) about 5 to about 40% PEG;
w) about 5 to about 30% PEG;
x) about 5 to about 20% PEG;
y) about 5 to about 10% PEG;
z) about 10 to about 50% PEG;
aa) about 10 to about 40% PEG;
ab) about 10 to about 30% PEG;
ac) about 10 to about 20% PEG;
ad) about 0.1% PEG;
ae) about 0.5% PEG;
af) about 1% PEG;
ag) about 2% PEG;
ah) about 3% PEG;
ai) about 4% PEG;
ak) about 5% PEG;
al) about 6% PEG;
am) about 7% PEG;
an) about 7.5% PEG;
ao) about 8% PEG;
ap) about 9% PEG;
aq) about 10% PEG;
ar) about 11% PEG;
as) about 12% PEG;
at) about 15% PEG;
au) about 20% PEG;
av) about 25% PEG;
aw) about 30% PEG;
ax) about 35% PEG;
ay) about 40% PEG;
az) about 45% PEG; and
ba) about 50% PEG.

17. The method of claim 1 wherein said chromatography media is contacted with PEG of an average molecular weight selected from the group consisting of:
a) 100 to about 20,000 daltons;
b) 100 to about 15,000 daltons;
c) 100 to about 10,000 daltons;
d) 100 to about 8,000 daltons;
e) 100 to about 6,000 daltons;
f) 100 to about 5,000 daltons;
g) 100 to about 4,000 daltons;
h) 100 to about 2,000 daltons;
i) 100 to about 1,000 daltons;
j) 100 to about 800 daltons;
k) 100 to about 600 daltons;
l) 100 to about 500 daltons;
m) 100 to about 400 daltons;
n) 100 to about 300 daltons;
o) 100 to about 200 daltons;
p) about 400 to about 20,000 daltons;
q) about 400 to about 15,000 daltons;
r) about 400 to about 10,000 daltons;
s) about 400 to about 8,000 daltons;
t) about 400 to about 6,000 daltons;
u) about 400 to about 5,000 daltons;
v) about 400 to about 4,000 daltons;
w) about 400 to about 2,000 daltons;
x) about 400 to about 1,000 daltons;
y) about 400 to about 800 daltons;
z) about 400 to about 600 daltons;
aa) about 400 to about 500 daltons;
ab) about 600 to about 20,000 daltons;
ac) about 600 to about 15,000 daltons;
ad) about 600 to about 10,000 daltons;
ae) about 600 to about 8,000 daltons;
af) about 600 to about 6,000 daltons;
ag) about 600 to about 5,000 daltons;
ah) about 600 to about 4,000 daltons;
ai) about 600 to about 2,000 daltons;
aj) about 600 to about 1,000 daltons;
ak) about 600 to about 800 daltons;
al) about 800 to about 20,000 daltons;
am) about 800 to about 15,000 daltons;
an) about 800 to about 10,000 daltons;
ao) about 800 to about 8,000 daltons;
ap) about 800 to about 6,000 daltons;
aq) about 800 to about 5,000 daltons;
ar) about 800 to about 4,000 daltons;
as) about 800 to about 2,000 daltons;
at) about 800 to about 1,000 daltons;
au) about 1,000 to about 20,000 daltons;
av) about 1,000 to about 15,000 daltons;
aw) about 1,000 to about 10,000 daltons;
ax) about 1,000 to about 8,000 daltons;
ay) about 1,000 to about 6,000 daltons;
az) about 1,000 to about 5,000 daltons;
ba) about 1,000 to about 4,000 daltons;
bb) about 1,000 to about 2,000 daltons;
be) about 4,000 to about 20,000 daltons;
bd) about 4,000 to about 15,000 daltons;
be) about 4,000 to about 10,000 daltons;
bf) about 4,000 to about 8,000 daltons;
bg) about 4,000 to about 6,000 daltons;
bh) about 4,000 to about 5,000 daltons;
bi) about 6,000 to about 20,000 daltons;
bj) about 6,000 to about 15,000 daltons;
bk) about 6,000 to about 10,000 daltons;
bl) about 6,000 to about 8,000 daltons;
bm) about 20,000 daltons;
bn) about 15,000 daltons;
bo) about 10,000 daltons;
bp) about 8,000 daltons;
bq) about 6,000 daltons;
br) about 5,000 daltons;
bs) about 4,000 daltons;
bt) about 2,000 daltons;
bu) about 1,000 daltons;
by) about 800 daltons;
bw) about 600 daltons;
bx) about 500 daltons;
by) about 400 daltons;
bz) about 300 daltons; and
ca) about 200 daltons.

* * * * *